(12) United States Patent
Washington

(10) Patent No.: US 6,858,021 B2
(45) Date of Patent: Feb. 22, 2005

(54) METHOD FOR DECREASING CATHETER-ASSOCIATED BACTERIURIA

(76) Inventor: Eric A. Washington, 846 Grant St., Gary, IN (US) 46404

( * ) Notice: Subject to any disclaimer, the term of this patent is extended or adjusted under 35 U.S.C. 154(b) by 77 days.

(21) Appl. No.: 10/248,734

(22) Filed: Feb. 13, 2003

(65) Prior Publication Data

US 2003/0158540 A1 Aug. 21, 2003

Related U.S. Application Data

(60) Provisional application No. 60/356,313, filed on Feb. 13, 2002.

(51) Int. Cl.[7] .................... A61M 25/00; A61M 27/00; A61M 5/32
(52) U.S. Cl. .................. 604/265; 604/544; 604/327
(58) Field of Search ................... 604/265, 544, 604/327, 199; 206/363; 427/2.3; 134/22.1

(56) References Cited

U.S. PATENT DOCUMENTS

| | | | | | |
|---|---|---|---|---|---|
| 1,772,975 | A | * | 8/1930 | Weiland ................ 514/557 |
| 4,296,747 | A | * | 10/1981 | Ogle ..................... 604/48 |
| 4,604,404 | A | * | 8/1986 | Munson et al. ......... 514/494 |
| 4,612,337 | A | * | 9/1986 | Fox et al. .............. 514/38 |
| 4,704,102 | A | * | 11/1987 | Guthery ................. 604/28 |
| 4,878,903 | A | * | 11/1989 | Mueller ................. 604/199 |
| 4,954,239 | A | * | 9/1990 | Mueller ................. 206/571 |
| 5,096,503 | A | * | 3/1992 | Wellman ............... 134/22.18 |
| 5,208,257 | A | * | 5/1993 | Kabara ................. 514/552 |
| 5,756,145 | A | * | 5/1998 | Darouiche ............. 427/2.24 |
| 5,819,331 | A | * | 10/1998 | Miuccio ................ 4/341 |
| 6,039,060 | A | * | 3/2000 | Rower ................... 134/167 R |
| 6,174,537 | B1 | * | 1/2001 | Khan .................... 424/405 |
| 6,187,768 | B1 | * | 2/2001 | Welle et al. ........... 514/199 |
| 6,306,422 | B1 | * | 10/2001 | Batich et al. .......... 424/423 |
| 6,333,424 | B1 | * | 12/2001 | Herczegh et al. ...... 558/159 |
| 6,408,861 | B1 | * | 6/2002 | Ortega ................... 134/100.1 |
| 6,526,603 | B1 | * | 3/2003 | Murphy ................. 4/480 |
| 6,638,978 | B1 | * | 10/2003 | Kabara ................. 514/550 |
| 2002/0007175 | A1 | * | 1/2002 | Chang ................... 604/544 |

* cited by examiner

*Primary Examiner*—Michael G. Bogart
(74) *Attorney, Agent, or Firm*—Gary M. Hartman; Domenica N.S. Hartman; Hartman & Hartman

(57) ABSTRACT

A method for reducing the incidence of urinary tract infection in a patient having an indwelling catheter, through the use of a weak acidic solution to treat the catheter drainage bag used by the patient. More particularly, the method decreases catheter-associated bacteriuria in a catheterized patient by the steps of instilling a sterile acetic acid solution (e.g., distilled vinegar) into the catheter drainage bag, dispersing the solution in the bag, and then draining the solution from the bag prior to resuming flow of urine from the patient into the bag.

20 Claims, 1 Drawing Sheet

METHOD FOR DECREASING CATHETER-ASSOCIATED BACTERIURIA

CROSS REFERENCE TO RELATED APPLICATIONS

This application claims the benefit of U.S. Provisional Application No. 60/356,313, filed Feb. 13, 2002.

BACKGROUND OF INVENTION

1. Field of the Invention

The present invention generally relates to techniques for reducing the incidence of urinary tract infections in patients with indwelling catheters, and more particularly to a method of using a weak acidic solution to treat a catheter drainage bag for reducing the incidence of such infections.

2. Description of the Related Art

Research data suggest that indwelling urethral catheters are the management techniques of choice for intractable urinary incontinence or chronic bladder outlet obstruction. The literature indicates that persistent, irreversible urinary incontinence may affect an estimated 50% of patients in tertiary care settings. However, patients who have an indwelling urinary catheter show a high incidence of urinary tract infections as demonstrated by numerous research studies. The catheterized urinary tract has been demonstrated to account for most nosocomial urinary tract infections with resulting bacteriuria. Complications of bacteriuria include obstructed catheters, acute pyelonephritis, bacteremia, periurethral purulent infections, vesicourethral reflux, chronic tubulointerstitial nephritis, chronic renal failure, and death. In addition, systemic symptoms of bacteriuria include fever above 38.4° C., nausea, vomiting, and costovertebral angle tenderness, as well as catheter-related hypovolemic sepsis. The literature supports nontreatment for asymptomatic bacteriuria. Long-term urethral catheterization has been linked with symptomatic bacteriuria (e.g., fever, costovertebral angle, or suprapubic tenderness). Notwithstanding, long-term urethral catheter-associated bacteriuria is said to be the most common nosocomial infection in secondary and tertiary care settings, as well as in home health care environments.

Research studies have indicated that about 40% of all nosocomial infections in the United States are associated with the urinary tract, of which 75% are related directly to indwelling catheterization. Bacteriuria has been demonstrated as a universal consequence of long-term urethral catheterization, where the majority of urinary tract infections occur through microbial ascension from the distal urethral tubule into the bladder cavity. The bladder normally resists infection by two known mechanisms: (1) mechanical factors (i.e., residual urine and the bladder urine volume) and (2) intrinsic factors (i.e., the antibacterial property of the bladder mucosa, urea concentration, osmolarity, and pH, as well as antimicrobial drugs). Factors that contribute to urinary tract infections include structural defects, systemic disorders, sexually transmitted diseases, insertion of a urethral catheter, and long-term indwelling catheterization. Urethral catheterization obliterates the natural cleansing of the urinary mucosa, encouraging the migration of pathogens into the bladder.

Antibiotic-resistant microorganisms are prevalent in long-term care facilities, and long-term indwelling catheters are convenient for transmission of antibiotic-resistant bacterial flora such as (in descending order of frequency) *Providencia stuartii*, *Proteus mirabilis*, *Morganella morganii*, Group D Streptococcus, *Staphylococcus aureus*, *Pseudomonas aeruginosa*, *Escherichia coli*, *Klebsiella pneumoniae*, *Entrococcus*, and *Entrobacter*. Moreover, research studies have found that antiseptic bladder irrigation did not prevent bacteriuria in patients with long-term catheters but, rather, promoted antibiotic-resistant microorganisms. Accordingly, routine antiseptic bladder irrigation was not recommended for patients with long-term indwelling catheters. Instead, patient education with regard to long-term catheterization has been recommended as an effective measure in reducing the incidence of catheter-related bacteriuria. However, education of patients by medical personnel appears to be inconsistent and not comprehensive, especially in the case of the elderly.

The available literature contains numerous reports with regard to decontamination of urinary drainage bags. However, the literature is unclear with respect to specific decontamination protocol in the acute or tertiary care setting. Various research reports indicated that following urinary bag decontamination, the incidence of bacteriuria continued. For example, Maizels and Schaeffer report in "Decreased Incidence of Bacteriuria Associated with Periodic Instillation of Hydrogen Peroxide into the Urethral Catheter Drainage Bag," J. Urol. 123:841–845 (1980), that in a randomized study of thirty-one acute spinal cord injury patients (analyzed according to the log rank and chi-square test) that bacterial contamination of the drainage bag could be eliminated effectively by instilling 30 ml of hydrogen peroxide every eight hours, with measurable cost savings to the patient and to the restorative care environment. Similarly, Holliman et al., "Controlled Trial of Chemical Disinfection of Urinary Drainage Bage", J. Urol. 60:419–422 (1987), reports a randomized study of fifty-seven patients, in which statistical analysis by t or chi-square test found a significant reduction ($P<0.05$) in catheter-associated urinary tract infections using 30 ml of hydrogen peroxide in drainage bags every eight hours. However, bacteria continued to be isolated from five of thirty bags. Notwithstanding, Sweet et al., "Evaluation of $H_2O_2$ Prophylaxis of Bacteriuria in Patients with Long-Term Indwelling Foley Catheters: A Randomized Controlled Study," Infect Control 6:263–266 (1985), suggested in a randomized study (N=238) tested by chi-square analysis, that instillation of $H_2O_2$ may cause a reduction of nosocomial urinary pathogens but no reduction in the rate of bacteriuria (i.e., the rate of bag contamination in the control group was 34% compared to 17% in the peroxide group, $P \leq 0.05$).

In a randomized study reported by Muncie et al., "Once-Daily Irrigation of Long-Term Urethral Catheters with Normal Saline," Arch. Intern. Med. 68:441–443 (1989), involving thirty-two long-term catheterized patients, routine, once-daily 30 ml normal saline irrigation, analyzed using the paired t test, showed no reduction of catheter obstructions or fevers. Meticulous daily perineal cleaning with soap and water and weekly drainage bag change by specially trained nursing personnel also did not decrease the incidence of urinary bag contamination.

Dille et al., "Increasing the Wearing Time of Vinyl Urinary Drainage Bags by Decontamination with Bleach," Arch Phys. Med. Rehabil. 74:431–437 (1993), in a randomized study of a two-group parallel design with a pretest and multiple post tests (N=54), analyzed by analysis of covariance and multiple analyses of covariance, showed that daily instillation of 15 ml of 5.25% sodium hypochlorite (household bleach) into urinary drainage bags and rinsed with 150 ml of tap water significantly reduced bacterial growth (0 to 100 colony-forming units (CFU's) per ml).

Similar findings were reported by Dille and Kirchhoff, "Decontamination of Vinyl Urinary Drainage Bags by Decontamination with Bleach," Rehabil. Nurs. 18:292–295 (1993), in a randomized study of fifty-four rehabilitation patients with neurogenic bladder dysfunction who required long-term catheterization. Dille and Kirchhoff found that daily decontamination of drainage bags with dilute bleach (5.25% sodium hypochlorite) demonstrated a 76.5% decrease in urinary bag bacterial growth (no bag cultures were greater than 50 CFU's/ml). However, bleach is a toxic agent, and incidental contact may cause skin irritation, clothing stains, metal corrosion, and harmful fumes if mixed with other disinfectants. Also, sodium hypochlorite is unstable and will dissipate when exposed to light if not used correctly.

In summary, the use of an indwelling catheter has been frequently associated with acute bacteriuria, regardless of strict adherence to urinary catheter care guidelines. The use of antibiotic bladder irrigation has been found to reduce the incidence of infection, but also shown to lead to the emergence of resistant organisms. Finally, while numerous researchers have attempted to reduce bacterial colonization within the collection bag by the instillation of various solutions, no researched agent or method has been shown to be effective in reducing the incidence of bacterial propagation within the catheter drainage bag. As such, a need persists for an improved method to reduce the incidence of urinary tract infections in patients with indwelling catheters.

SUMMARY OF INVENTION

The present invention provides a method for reducing the incidence of urinary tract infection in a patient having an indwelling catheter, through the use of a weak acidic solution to treat the catheter drainage bag used by the patient. More particularly, the method decreases catheter-associated bacteriuria in a catheterized patient by the steps of instilling a sterile acetic acid solution (e.g., distilled vinegar) into the catheter drainage bag, dispersing the solution in the bag, and then draining the solution from the bag. Thereafter, urine is allowed to flow from the catheterized patient through a catheter and into the bag.

According to a preferred aspect of the invention, a significant advantage of this invention is that distilled vinegar, which is inexpensive, widely available and nontoxic, is able to substantially reduce both the type and number of colony-forming bacteria in a catheter drainage receptacle. As a result, the treatment method of this invention is particularly beneficial to patients with long-term indwelling urethral catheters by decreasing a patient's risk in polymicrobial bacterial propagation within the catheter drainage system, such that the incidence of catheter-acquired bladder bacteriuria can be reduced.

Other objects and advantages of this invention will be better appreciated from the following detailed description.

DETAILED DESCRIPTION

Figure 1:
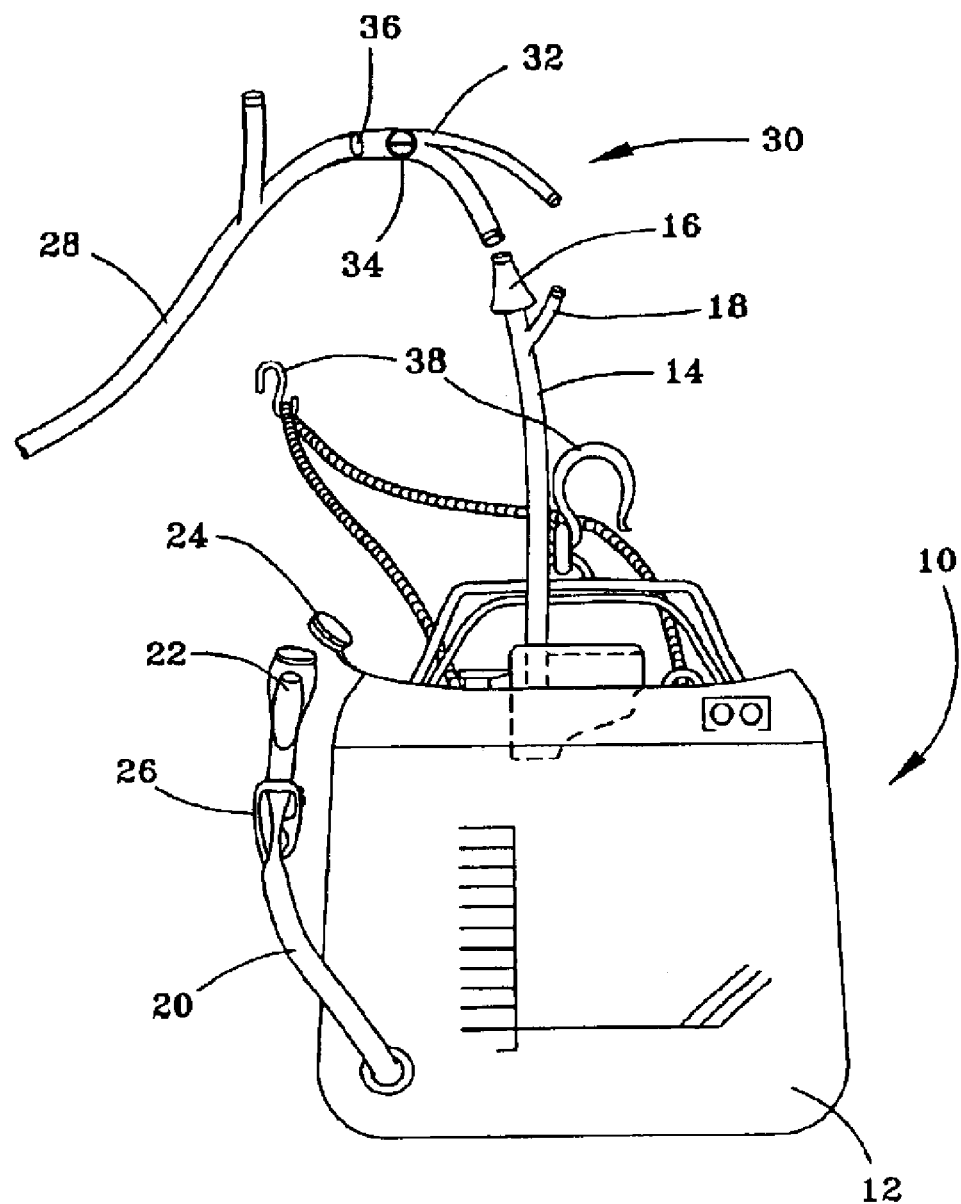
FIG. 1 is a schematic representation of a urinary collection bag suitable for use with the present invention.

A research study leading to the present investigation was carried out to investigate whether the one-time instillation and drainage of certain treatment solutions into a urinary drainage bag could significantly reduce polymicrobial bacteriuria colonization and subsequent microbial propagation into the bladder in long-term catheterized populations, as measured at twenty-four hour intervals over three days.

Key variables investigated were the types of irrigation solution evaluated and the types and levels of bacteria found in a treated catheter drainage bag, at twenty-four hour intervals of incubation, during treatment conditions. The type of irrigation solution used constituted the independent variable. The irrigation solutions were sterile hydrogen peroxide and sterile distilled vinegar (as used herein, containing about 5 wt. % acetic acid). Hydrogen peroxide ($H_2O_2$), used herein in a 3% aqueous solution, is germicidal and an effective cleaning agent. Hydrogen peroxide decomposes rapidly when exposed to light or organic matter. Vinegar is a weak acetic acid solution derived from alcohol by the action of Acetobacter. Vinegar is distilled to remove color and other impurities, yielding what is referred to as white vinegar. Generally, properties of distilled (white) vinegar include: (1) actively microbicidal; (2) not highly irritating, toxic, or malodorous; (3) not corrosive and does not stain or discolor; (4) readily soluble, and stable in the presence of organic matter; (5) relatively inexpensive; and (6) an acetic acid content of typically between about 4 and 8 weight percent.

The dependent variables of the investigation were the types and levels of bacteria in the drainage bag, at twenty-four hour intervals of incubation, during treatment conditions. A certified laboratory was contracted to determine the germicidal values of the solutions tested. After twenty-four hours of incubation at about 37° C., (room temperature), bacterial growth was recorded at twenty-four hour intervals. Laboratory protocol for reporting types and number of bacteria provided results by identification of the organism by species present in the specimen.

For the study, a total of fifty-seven subjects were initially identified to participate in the study: fifteen from three hospitals and forty-two from ten skilled nursing facilities. Of these, thirty-seven patients were not included in the study due to exclusion criteria or institutional denial. Patients who were febrile, acutely ill, receiving antibiotic therapy, or with symptoms of urinary tract infection were excluded based on a review of the patient's chart. Patients with other methods of urinary drainage, such as condom catheter drainage, superpubic catheterization, and intermittent urethral catheterization, were not considered. Moreover, because of the chance of cross-infection, infected and uninfected patients with indwelling urinary catheters who shared the same room or adjacent beds were not considered. Each of the twenty remaining patients (from five independent skilled care facilities) had a long-term indwelling urethral (Foley) catheter (i.e., catheterized more than thirty days; because agency protocol mandated catheter replacement every three months, each subject's catheter had been in place not longer than ninety days). The subjects' mean age was 69.9 years, with a range of forty-three to ninety-two years. Twelve patients were women and eight were men. Nine patients were Caucasian, nine were African American, and two were Hispanic. A variety of primary diagnoses were identified, with neurogenic bladder secondary to a neurophysiologic deficit being most common. None of the patients had to be withdrawn from the study due to catheter-associated bacteriuria or febrile illness.

The patients were randomly assigned to three experimental groups: one group was designated a control group whose catheter drainage bags were not treated with an irrigation solution; the drainage bags of the remaining groups were treated with one of the two irrigation solutions investigated. The methods of data collection were verified prior to the commencement of the study by use of a literature review and institutional review board pre approval. All urine collection was made between 5:00 A.M. and 6:30 A.M. The urine specimens were promptly refrigerated and transported to the microbiology laboratory. Organisms and colony counts were identified by standard laboratory methods.

The research approach carried out in the study comprised four primary steps: (1) collection of urine from the catheter drainage bags for baseline cultures; (2) instillation of the irrigation solution into the drainage bags; (3) collection of urine from the drainage bags at 24-hour intervals; and (4) evaluation of the results of bacterial growth at 24-hour intervals. The initial concentration of bacteria in each drainage bag was determined prior to instillation of the irrigation solution. With regard to the patients in the groups whose drainage bags were treated with hydrogen peroxide or distilled vinegar, the drainage bags (approximate filled volume of about 50 to 150 ml) were emptied of any residual urine, after which the distal segment of the Foley catheter was clamped to avoid any possibility of reagent reflux into the patient's bladder. The proximal port of the catheter tubue was then cleansed with alcohol and injected with a one-time dose of about 50 ml of either sterile 3% hydrogen peroxide or sterile distilled vinegar (about 5 wt. % acetic acid solution), both of which were at approximately room temperature when instilled. The instilled irrigation solution was gently dispersed throughout the drainage bag for about thirty seconds and then drained from the bag. The Foley catheter was then unclamped and the drainage bag placed in a dependent position.

Urine samples were obtained from the drainage bags of all subjects at twenty-four hour intervals over four days. All urine specimens were aseptically collected and taken to the contracted laboratory for culture and analysis. Facility policy on infection control was reviewed to determine and comply with any institutional requirements with regard to infection control or subjects' participation. Hand washing was performed immediately before and after any manipulation of the catheter site or apparatus.

The comparative performance of the hydrogen peroxide and distilled vinegar irrigation solutions on organism type and colony counts was tested using analysis of variance with significance set at an alpha level of 0.05. (In the following tables, the F-Ratio (or F-Value) and P-Value have their ordinary meaning: F-Ratio—the measurement of distance between individual distributions; P-Value—the probability value. As the F-Ratio goes up, the P-Value goes down, i.e., more confidence in there being a difference between two means.) Table 1 indicates differences identified between the three groups in the mean number of different types of organisms identified at each of the four twenty-four-hour collection intervals. As apparent from Table 1, only at the forty-eight-hour interval were significant differences found between the three groups in types of organisms. Post hoc analysis indicated that the distilled vinegar group had a significant loss of different types of organisms compared to the control group at forty-eight hours after instillation. There was no statistically significant difference between the hydrogen peroxide and control groups, or between the hydrogen peroxide and distilled vinegar groups.

TABLE I

| Time | Control | Hydrogen Peroxide | Distilled Vinegar | F-Ratio | P-Value |
|---|---|---|---|---|---|
| 00 h | 2.5 | 2.6 | 2.3 | 0.3569 | 0.70 |
| 24 h | 2.7 | 2.3 | 2.7 | 0.2335 | 0.79 |
| 48 h | 2.7 | 2.1 | 1.1 | 5.7501 | 0.013 |
| 72 h | 2.0 | 1.5 | 1.8 | 0.5580 | 0.24 |

Table 2 evidences the differences between the three groups in terms of the mean values for categories of colony count, where a score of "3" was given to the category of >100,000, a score of "2" was given to a colony count of 10,000 to 100,000, and a score of "1" was given to a colony count of <10,000.

TABLE II

| Time | Control | Hydrogen Peroxide | Distilled Vinegar | F-Ratio | P-Value |
|---|---|---|---|---|---|
| 00 h | 6.6 | 6.2 | 6.7 | 0.0907 | 0.91 |
| 24 h | 7.3 | 5.6 | 6.5 | 0.4488 | 0.64 |
| 48 h | 7.2 | 5.3 | 3.0 | 7.2462 | 0.006 |
| 72 h | 5.2 | 3.8 | 4.6 | 1.6435 | 0.22 |

Post hoc analysis indicated that the distilled vinegar group had significantly fewer colonies of bacteria than the control group at forty-eight hours after instillation. There was no statistically significant difference between the hydrogen peroxide and control groups, or between the hydrogen peroxide and distilled vinegar groups (analysis of variance, P=0.03 and P=0.006 with regard to types of microorganisms and aggregate colony counts, respectively). Nevertheless, the results of comparative performance of hydrogen peroxide and distilled vinegar shown in Tables 1 and 2 suggest a strong correlation between instillation of distilled vinegar and decreased bacteriuria. While both irrigation solutions decreased bacterial contamination of the urinary drainage bag when compared to the control group, results obtained from the forty-eight-hour collection interval evidenced that the distilled vinegar group exhibited a significant reduction in drainage bag bacteriuria as compared to the hydrogen peroxide group, at a level of 0.0059 by analysis of variance.

Table 3 shows the types of organisms identified in all drainage bags, in descending order of prevalence, during the full course of the study, and represents a relationship between the growth of the individual bacterium and the growth of bacterial density in culture. That is, bacterial growth will continue unhindered at an exponential rate up to its maximum value, which may be considered characteristic of the particular bacterial strain given the particular culture medium.

TABLE III

| Number of Patients | Organisms Isolated |
|---|---|
| 14 | *Staphylococcus epidermidis* |
| 11 | *Proteus marablis* |
| 10 | *Streptococcus faecalis* |
| 7 | *Pseudomonas aeruginosa* |
| 4 | *Escherichia coli* |
| 2 | Enterococcus |
| 2 | Yeast |
| 1 | Corynebacterium |
| 1 | Lactobacillus |

The data obtained from this study suggest that there is a significant difference after forty-eight hours in the bactericidal properties of hydrogen peroxide and distilled vinegar when used as aseptic management in conventional catheter drainage bag systems. While previous research has attempted to reduce the incidence of catheter drainage bag bacteriuria in long-term urethral catheterization through the instillation of assorted disinfectants, such as hydrogen peroxide and sodium hypochlorite, such previous efforts evidenced that bacteriuria continued to occur predominantly in the catheter drainage bag. In contrast, the study leading to the present invention evidenced a significant difference between nontreatment (the control group) and the use of sterile distilled vinegar as a drainage bag irrigation solution, on the basis that distilled vinegar was able to substantially reduce both the type and number of colony-forming bacteria in a catheter drainage receptacle. This performance was gauged in terms of the number of urinary isolates among different colonies of bacterial species present in the urinary drainage bags, at twenty-four hour intervals, during the collection of the urine specimens for culture. Notably, only the forty-eight-hour collection interval showed statistical significance in the reduction of drainage bag bacteriuria, which may be related to the acidic nature of vinegar. That is, the protein molecular structure, essential for bacterial cell functioning, is disrupted when exposed to an acidic environment. On this basis, it is believed that distilled vinegar (or another suitable source of acetic acid) should be effective as an irrigation solution for catheter drainage receptacles.

While the prior art has shown that intermittent instillation of hydrogen peroxide into urinary drainage bags is efficacious in preventing both bacterial contamination of catheter drainage bags and catheter-associated bacteriuria, "bag source" bacteriuria continued to be reported as a significant problem for drainage bags treated with hydrogen peroxide. In contrast, the present invention evidences that the instillation of distilled vinegar into urinary drainage bags may result in a significant reduction in the type and number of certain kinds of microorganisms in catheter drainage bags.

The present invention has broad implications for nurse researchers and clinicians, as well as administrators and manufacturers of urethral catheters. The high prevalence and serious problems associated with catheter bag bacteriuria must be addressed by nurses in all practice settings. In the past, nursing practice concerning the urine drainage system has focused on patient education, bag changing, hand washing, and/or discontinuation of indwelling catheterization. While these practices are invaluable, the present offers an additional and valuable step in reducing catheter bag bacteriuria.

In view of the present invention, catheter drainage bag design should also be considered. Current urine drainage systems do not adequately permit periodic catheter irrigation or an appropriate hygienic change from drainage bag to leg bag. A bag design that may permit both is shown in FIG. 1 as allowing for the convenient instillation of a distilled vinegar irrigation solution (or other antimicrobial agent) as well as decreased cross-contamination during changing of the collection receptacle. The design shown in FIG. 1 comprises a collection bag 10, which includes a molded base hollow 12 and a flexible rubber or soft plastic drainage tube 14 with a proximal connector 16 and a distal irrigation port 18 for instilling the irrigation solution. The collection bag 10 is preferably made of a soft antimicrobial vinyl and preferably has an approximate capacity of about 2500 ml. A threaded plastic drainage tube 20 for emptying urine collected in the bag 10 is molded at a bottom corner of the bag 10 and includes an anti-reflux drain spigot 22, a microbicidal cap 24 and a drain clamp 26. FIG. 1 also shows a catheter 28, preferably made of a soft antimicrobial plastic or rubber, as having a dual proximal lumen 30. A dual flexible interconnector 32 with a turn dial 34 is located at the catheter bifurcation to enable the catheter 28 to switch from a collection bag application to a leg bag utility. A urine collection port 36 distal to the turn dial 34 permits the withdrawal or instillation of fluids. Connectors 38 permit the collection bag 10 to be mounted to a bed in a conventional manner. The urinary drainage system depicted in FIG. 1 has the potential for also reducing catheter-associated urinary tract infections and the nosocomial spread of bacteria.

While a one-time instillation of about 50 ml of distilled vinegar was used in the investigation, it is foreseeable that more or less frequent treatments, e.g., daily instillations, of greater or lesser amounts of sterile distilled vinegar (or another source of acetic acid) could also be clinically beneficial to patients with long-term indwelling urethral catheters. To provide the benefits of this invention, an effective amount of the instilled solution is generally that which will coat the entire interior of the collection bag and its drainage tubules. As such, the amount of solution necessary to reduce the incidence of bacterial growth and its subsequent propagation into the bladder will depend in part of the capacity of the bag. However, it is believed that a standard instillation dose of about thirty to about fifty ml is sufficient to lower bacterial colony counts below pathogenic levels, with the use of higher doses being foreseeable. Using such solutions to reduce bacterial colony count within a drainage bag, that is, decreasing a patient's risk in polymicrobial bacterial propagation within the catheter drainage system, can reduce the incidence of catheter-acquired bladder bacteriuria. In any event, an important conclusion that can be drawn from the study reported above is that urethral catheter bag bacteriuria is strongly associated with long-term indwelling catheter use.

While the invention has been described in terms of a preferred embodiment, it is apparent that other forms could be adopted by one skilled in the art. Therefore, the scope of the invention is to be limited only by the following claims.

What is claimed is:

1. A method for decreasing catheter-associated bacteriuria in a catheterized patient having an urethral catheter fluidically connected to a catheter drainage bag, the method comprising the steps of:

while the catheterized patient remains connected to the catheter, clamping a portion of the catheter to prevent any contents within the bag from entering a distal segment of the catheter;

instilling a sterile acetic acid solution into the bag;

dispersing the solution in the bag;

draining the solution from the bag; and then unclamping the portion of the catheter to allow urine to flow from the catheterized patient through the catheter and into the bag.

2. The method according to claim 1, wherein the clamping, instilling, dispersing, draining, and unclamping steps are repeated approximately every forty-eight hours.

3. The method according to claim 1, wherein the clamping, instilling, dispersing, draining, and unclamping steps are repeated approximately every twenty-four hours.

4. The method according to claim 1, wherein the solution contains about 4 to about 8 weight percent acetic acid.

5. The method according to claim 1, wherein the solution contains about 5 weight percent acetic acid.

6. The method according to claim 1, wherein the solution is vinegar.

7. The method according to claim 6, wherein the instilling step comprises instilling an amount of the solution effective to decrease bacterial growth and/or colonization in the bag.

8. The method according to claim 7, wherein the instilling step comprises instilling about fifty milliliters of the solution into the bag.

9. The method according to claim 1, wherein the solution is at approximately room temperature when instilled.

10. The method according to claim 1, further comprising the step of emptying the bag before clamping the portion of the catheter.

11. The method according to claim 1, wherein the instilling step comprises injecting the sterile acetic acid solution into the bag through a port located between the portion of the catheter and the bag.

12. The method according to claim 1, further comprising the steps of providing the catheter with first and second lumens and providing means for selectively connecting and disconnecting the first and second lumens to a tube fluidically attached to the bag.

13. The method according to claim 12, wherein the sterile acetic acid solution is instilled into the bag through a port on the tube fluidically attached to the bag.

14. A method for decreasing catheter-associated bacteriuria in a patient having an indwelling urethral catheter, the method comprising the steps of:

cleansing a proximal port located between the portion of the catheter and the bag;

injecting a sterile distilled vinegar into the bag through the proximal port, the vinegar being injected in an amount effective to decrease bacterial growth and/or colonization in the bag;

dispersing the vinegar in the bag;

draining the vinegar from the bag;

unclamping the portion of the catheter, and then placing the bag in a dependent position to receive urine through the catheter.

15. The method according to claim 14, wherein the steps of the method are repeated in sequence approximately every forty-eight hours.

16. The method according to claim 14, wherein the steps of the method are repeated in sequence approximately every twenty-four hours.

17. The method according to claim 14, wherein the vinegar contains about 4 to about 8 weight percent acetic acid.

18. The method according to claim 14, wherein the vinegar contains about 5 weight percent acetic acid.

19. The method according to claim 14, wherein the injecting step comprises injecting about fifty milliliters of the vinegar into the bag.

20. The method according to claim 14, wherein the vinegar is at approximately room temperature when injected.

emptying a catheter drainage bag fluidically connected to the catheter;

clamping a portion of the catheter to prevent any contents of the bag from entering a distal segment of the catheter;

* * * * *